United States Patent
Hong

(10) Patent No.: US 10,362,987 B2
(45) Date of Patent: Jul. 30, 2019

(54) APPARATUSES AND METHODS FOR MONITORING MEDICATION-TAKING STATUS

(71) Applicant: Ziqiang Hong, Irving, TX (US)

(72) Inventor: Ziqiang Hong, Irving, TX (US)

(73) Assignee: Ziqiang Hong, Irving, TX (US)

( * ) Notice: Subject to any disclaimer, the term of this patent is extended or adjusted under 35 U.S.C. 154(b) by 0 days.

(21) Appl. No.: 15/397,736

(22) Filed: Jan. 4, 2017

(65) Prior Publication Data
US 2018/0184971 A1     Jul. 5, 2018

(51) Int. Cl.
| | |
|---|---|
| *A61J 7/04* | (2006.01) |
| *A61B 5/00* | (2006.01) |
| *A61J 7/02* | (2006.01) |
| *B65D 51/24* | (2006.01) |
| *A61B 5/0205* | (2006.01) |
| *A61B 5/0402* | (2006.01) |
| *G06F 19/00* | (2018.01) |
| *A61B 5/021* | (2006.01) |

(Continued)

(52) U.S. Cl.
CPC ........ *A61B 5/4833* (2013.01); *A61B 5/02055* (2013.01); *A61B 5/0402* (2013.01); *A61B 5/4869* (2013.01); *A61J 7/02* (2013.01); *A61J 7/0418* (2015.05); *B65D 51/245* (2013.01); *G06F 19/3462* (2013.01); *A61B 5/021* (2013.01); *A61B 5/087* (2013.01); *A61B 5/14532* (2013.01); *A61B 2562/227* (2013.01); *A61J 2200/30* (2013.01); *A61J 2200/74* (2013.01)

(58) Field of Classification Search
CPC .. G06F 19/34; G06F 19/3456; G06F 19/3462; A61J 1/00; A61J 1/03; A61J 7/02; A61J 7/04; A61J 7/0409; A61J 7/0427; A61J 7/0436; A61J 7/0481; A61J 7/049; A61J 2200/30; A61J 2200/70; A61J 2200/74; G08B 21/24
See application file for complete search history.

(56) References Cited

U.S. PATENT DOCUMENTS

| | | | |
|---|---|---|---|
| 4,504,153 A | * | 3/1985 | Schollmeyer ......... A61J 7/0481 221/2 |
| 6,294,999 B1 | | 9/2001 | Yarin et al. |

(Continued)

*Primary Examiner* — Andrew W Bee
(74) *Attorney, Agent, or Firm* — Haojin Wang

(57) ABSTRACT

In accordance with one example embodiment of the present disclosure, an apparatus for monitoring a medication-taking status is disclosed. The apparatus is configured as part of or coupled with a medication container. The apparatus includes a first sensor that is disposed inside the apparatus, activated upon a detection by a second sensor of a motion of the medication container, or a non-motion of the medication container for a predefined time period, and configured to measure medication pills stored in the medication container. The apparatus also includes a control module configured to determine the medication-taking status based on the measurement of the medication pills. The apparatus further includes a communication module that is disposed inside the apparatus and configured to transmit at least one of a report and a warning message based at least in part on the medication-taking status to at least one remote subscriber.

19 Claims, 9 Drawing Sheets

(51) Int. Cl.
     *A61B 5/145*          (2006.01)
     *A61B 5/087*          (2006.01)

(56)                References Cited

U.S. PATENT DOCUMENTS

| | | | |
|---|---|---|---|
| 6,401,991 B1* | 6/2002 | Eannone | A61J 7/0481 |
| | | | 221/103 |
| 2008/0105588 A1 | 5/2008 | Tran | |
| 2010/0283601 A1 | 11/2010 | Tai et al. | |
| 2013/0222135 A1* | 8/2013 | Stein | A61J 7/0409 |
| | | | 340/540 |
| 2014/0276476 A1* | 9/2014 | Fateh | G08B 21/02 |
| | | | 604/290 |
| 2015/0095047 A1* | 4/2015 | Burrows | G06F 19/3456 |
| | | | 705/2 |
| 2016/0015602 A1* | 1/2016 | Panzini | A61J 7/0481 |
| | | | 340/666 |
| 2016/0327427 A1* | 11/2016 | Briones | A61J 7/02 |
| 2016/0354283 A1* | 12/2016 | Cho | A61J 7/02 |
| 2017/0018166 A1* | 1/2017 | Johnson | G08B 21/24 |
| 2017/0095405 A1* | 4/2017 | Afsarifard | A61J 7/0418 |
| 2017/0232204 A1* | 8/2017 | Knapp | A61M 5/31568 |
| | | | 604/66 |
| 2017/0286633 A1* | 10/2017 | Ashoori | G16H 40/63 |
| 2017/0351838 A1* | 12/2017 | Chen | G06F 19/3456 |

\* cited by examiner

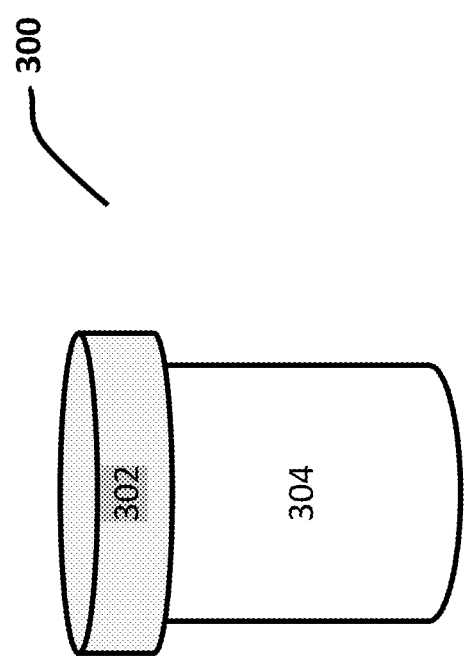

APPARATUSES AND METHODS FOR MONITORING MEDICATION-TAKING STATUS

BACKGROUND

Field

Aspects of the present disclosure relate generally to personal health care monitoring system, and more particularly to methods and apparatuses for monitoring medication-taking status.

Background

Medication non-compliance is a major problem in healthcare, according to various studies. Physicians prescribe medications for a large number of chronic, asymptomatic diseases. These medications must typically be taken daily for the rest of the patient's life in order to sustain quality of life and reduce health risks. Typical examples of diseases in this class include hypertension, hypercholesterolemia and osteoporosis. With many such diseases, a patient feels no different, whether or not they take their medication in accordance to a prescribed regiment or a prescription. So, unlike medication for an acute internal or external injury, there are no apparent short-to-medium term costs or effect for non-compliance. This presents a challenge even for those patients who want to comply, let alone those who need a helping hand.

There are conventional systems that track a patient's behavior in order to determine whether or not to issue a non-compliance alert in response to a non-compliance. The tracking or monitoring systems are often complicated to operate and use. For example, docking station based systems require that a user or patient must go to a stationary docking station that dispenses the medication and monitors the medication taking status (see US2010/0100237 and U.S. Pat. No. 6,183,417, for example). Thus, there is a need for a simple medication-taking status monitoring system that is mobile, and part of the medication container itself.

SUMMARY

According to one aspect of the present disclosure, an apparatus for monitoring a medication-taking status is configured as a part of or coupled with a medication container. The apparatus includes a first sensor that is disposed inside the apparatus, activated upon a detection by a second sensor of a motion of the medication container, or a non-motion of the medication container for a predefined time period, and configured to measure medication pills stored in the medication container. The apparatus also includes a control module configured to determine the medication-taking status based on the measurement of the medication pills. The apparatus further includes a communication module that is disposed inside the apparatus and configured to transmit at least one of a report and a warning message based at least in part on the medication-taking status to at least one remote subscriber.

According to another aspect, a method for monitoring a medication-taking status by a monitoring apparatus at a medication container includes activating a first sensor upon detection by a second sensor of a motion of the medication container, or a non-motion of the medication container for a prescribed time period. The method also includes measuring medication pills stored in the medication container by the first sensor upon activation of the first sensor and determining the medication-taking status based at least in part on the measurement of the medication pills from the first sensor. The method further includes transmitting at least one of a report and a warning message based at least in part on the medication-taking status to at least one remote subscriber.

According to yet another aspect of the present disclosure, an apparatus for monitoring a medication-taking status for a medication container, comprises a memory and at least one processor coupled to the memory. The at least one processor is configured to activate a first sensor upon detection by a second sensor of a motion of the medication container, or a non-motion of the medication container for a predefined time period. The at least one processor is further configured to measure medication pills stored in the medication container by the first sensor upon activation of the first sensor. The at least one processor is further configured to determine the medication-taking status based at least in part on the measurement of the medication pills from the first sensor; and transmit at least one of a report and a warning message based at least in part on the medication-taking status to at least one remote subscriber.

This has outlined, rather broadly, the features and technical advantages of the present disclosure in order that the detailed description that follows may be better understood. Additional features and advantages of the disclosure will be described below. It should be appreciated by those skilled in the art that this disclosure may be readily utilized as a basis for modifying or designing other structures for carrying out the same purposes of the present disclosure. It should also be realized by those skilled in the art that such equivalent constructions do not depart from the teachings of the disclosure as set forth in the appended claims. The novel features, which are believed to be characteristic of the disclosure, both as to its organization and method of operation, together with further objects and advantages, will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

The features, nature, and advantages of the present disclosure will become more apparent from the detailed description set forth below when taken in conjunction with the drawings in which like reference characters identify correspondingly throughout.

FIG. 3 provides a block diagram for a structural view of yet another example medication container, according to one aspect of the present disclosure.

DETAILED DESCRIPTION

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will be apparent to those skilled in the art that these concepts may be practiced without these specific details. In some instances, well-known structures and components are shown in block diagram form in order to avoid obscuring such concepts.

The term "medication pill," as used throughout the disclosure, generally refers to a variety of shapes, forms and colors of medications, including but not limited to traditional pill, capsule gel, tablet, caplet, and the like. The term "user" of a medication container generally refers to a person who uses or accesses the medication container to takes medication. Examples of such a user may include a patient, elderly with medical needs, or a care giver.

Figure 1:
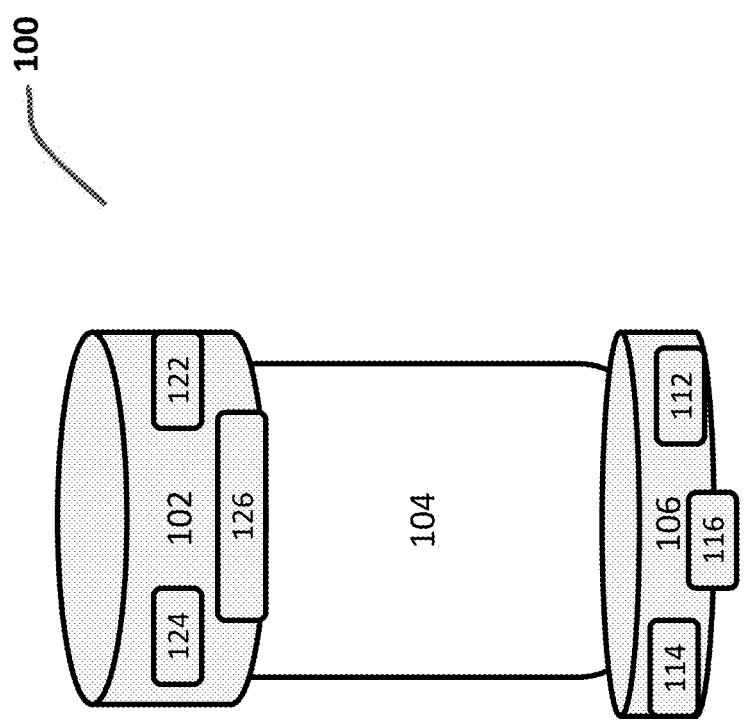
FIG. 1 provides a block diagram for a structural view of an example medication container, according to one aspect of the present disclosure.

FIG. 1 provides a structural view of a medication container 100, according to one aspect of the present disclosure. The medication container 100 includes a container body 104 and a medication-taking status monitoring apparatus configured as a cap 102 and a base 106 of the medication container 100. The cap 102 may include a warning buzzer 124, a display 126, and a local communication module 122. In one example embodiment, the buzzer 124 may emit a warning buzzer sound when the user of the medication container fails to take any medication according to an active prescription or a current medication regiment.

The display 126 may display texts to the user. The texts may include a reminder to the user for taking medication or information from the active prescription or the current regiment. The display 126 may also display a time, a date and day when there are not any warning message to be displayed. The communication module 122 is for communicating with the base 106 of the medication container 100. In one aspect, the communication module 122 may be a Bluetooth transceiver, a WiFi transceiver, a near-field, short range wireless transceiver or a wired transceiver.

The cap 102 may be coupled to the medication container body 104 in a variety of ways. For example, the coupling mechanism may be coupling threads, a clip-on container-cap lock, or a coupling clinch. The medication container body 104 for holding medication pills may take a variety of shapes, such as cylinder and square, and may be made of different materials, such as plastic, glass and metal.

In one example scenario, the cap 102 is assembled with the medication container body 104 at a medication distributor's facility such as a pharmacy. In another example scenario, a user may use the medication container cap 102 in place of an existing regular cap of a medication container that the user has used before. In this example scenario, the user may make a regular medication container a "smart" medication container by replacing an existing cap with the cap 102.

The base 106 of the medication container 100 may include a sensor module 114, a communication module 112, and a connection port module 116, among other components. The sensor module 114 may include one or more sensors. The example sensors may include a micro weight sensor to measure a weight of the medication pills and a gyro sensor to detection motion or non-motion of the medication container. The communication module 112 may include one or more of a Bluetooth transceiver, a WiFi transceiver, a near-field, short range wireless transceiver, or a wired transceiver. The communication module 112 is for communicating with the cap 102. In addition, the communication module 112 may also communicate with a local wireless server such as a WiFi access point, and then a remote Internet cloud server via the access point.

The connection port module 116 may include one or more connection ports and may connect the medication container 100 to one or more of other measurement devices. The other measurement devices may include, but are not limited to a blood pressure measurement device, a blood glucose level measurement device, a body temperature thermostat, a body weight and body composition measurement device, a lung function testing spirometer device, and an electrocardiography (ECG) device. In one example aspect, a connection port may be a serial port, a USB port, or an audio port. The connection port module 116 may be connected to the measurement devices via a wireless connection or a wired connection. An example wired connection may include a micro USB connection and a mini USB connection.

Figure 2:
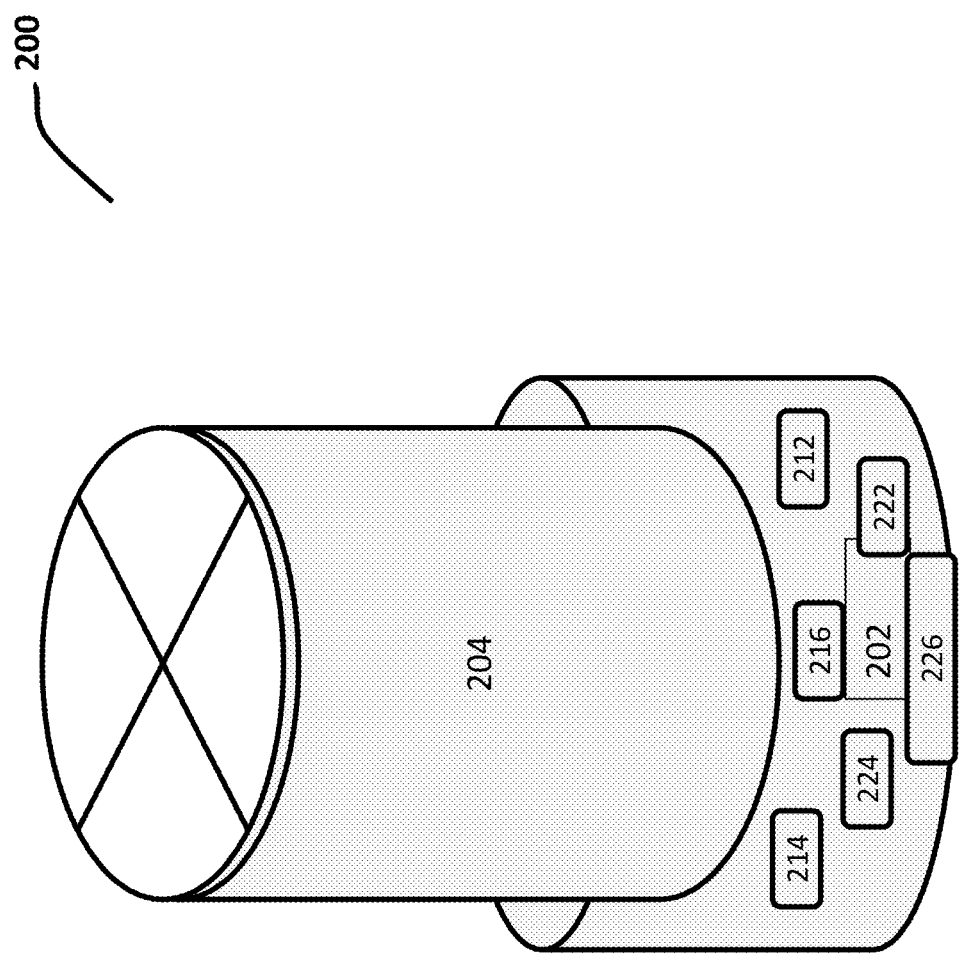
FIG. 2 provides a block diagram for a structural view of another example medication container, according to one aspect of the present disclosure.

FIG. 2 provides a structural view of an example medication container 200, according to one aspect of the present disclosure. The medication container 200 includes a medication container body 204 and a medication-taking status monitoring apparatus configured a medication container base 202. The medication container base 202 may include a warning buzzer 224 that is similar to the warning buzzer 124, a display 226 that is similar to the display 126, and a communication module 222 that is similar to the communication module 122 of FIG. 1. The medication container base 202 may also include a sensor module 214 that is similar to the sensor module 114, and a connection port module 216 that is similar to the connection port module 116, among other components.

The medication container base 202 may be coupled to the medication container body 204 in a variety of ways. For example, the coupling mechanism may include coupling threads, a clip-on container-cap lock, a coupling clinch, and a silicon ring. The medication container body 204 for holding medication pills may take a variety of shapes such as cylinder and square, and may be made of different materials, such as plastic, glass or metal.

In one example scenario, the medication container base 202 is assembled with the medication container body 204 at a medication distributor's facility such as a pharmacy or a clinic. In another example scenario, a user may attach an existing medication container to the base 202 with no or little further manual intervention.

FIG. 3 provides a structural view of a medication container 300, according to one aspect of the present disclosure. The medication container 300 includes a medication container body 304 and a medication-taking status monitoring apparatus configured as a cap 302. The cap 302 may include a warning buzzer (not shown) that is similar to the warning buzzer 224, a display (not shown) that is similar to the display 226, and a communication module (not shown) that is similar to the communication module 222. The cap 302 may also include a sensor module (not shown) that is similar to the sensor module 214, and a connection port module (not shown) similar to the connection port module 216, among other components The cap 302 may be coupled to the medication container body 104 in a variety of ways. For example, the coupling mechanism may include coupling threads, a clip-on container-cap lock, or a coupling clinch. The medication container body 304 for holding medication pills may take a variety of shapes such as cylinder and square, and may be made of different materials, such as plastic, glass or metal.

In one example scenario, the cap 302 is assembled with the medication container body 304 at a medication distributor's facility such as a pharmacy or a clinic. In another example scenario, a user may use the cap 102 in place of an existing regular cap of a medication container that the user has used before. In this example scenario, the user may make a regular medication container a "smart" one by replacing an existing cap with the cap 102.

Figures 4A, 4B, 4C, 4D, 4E, 4F, 4G:
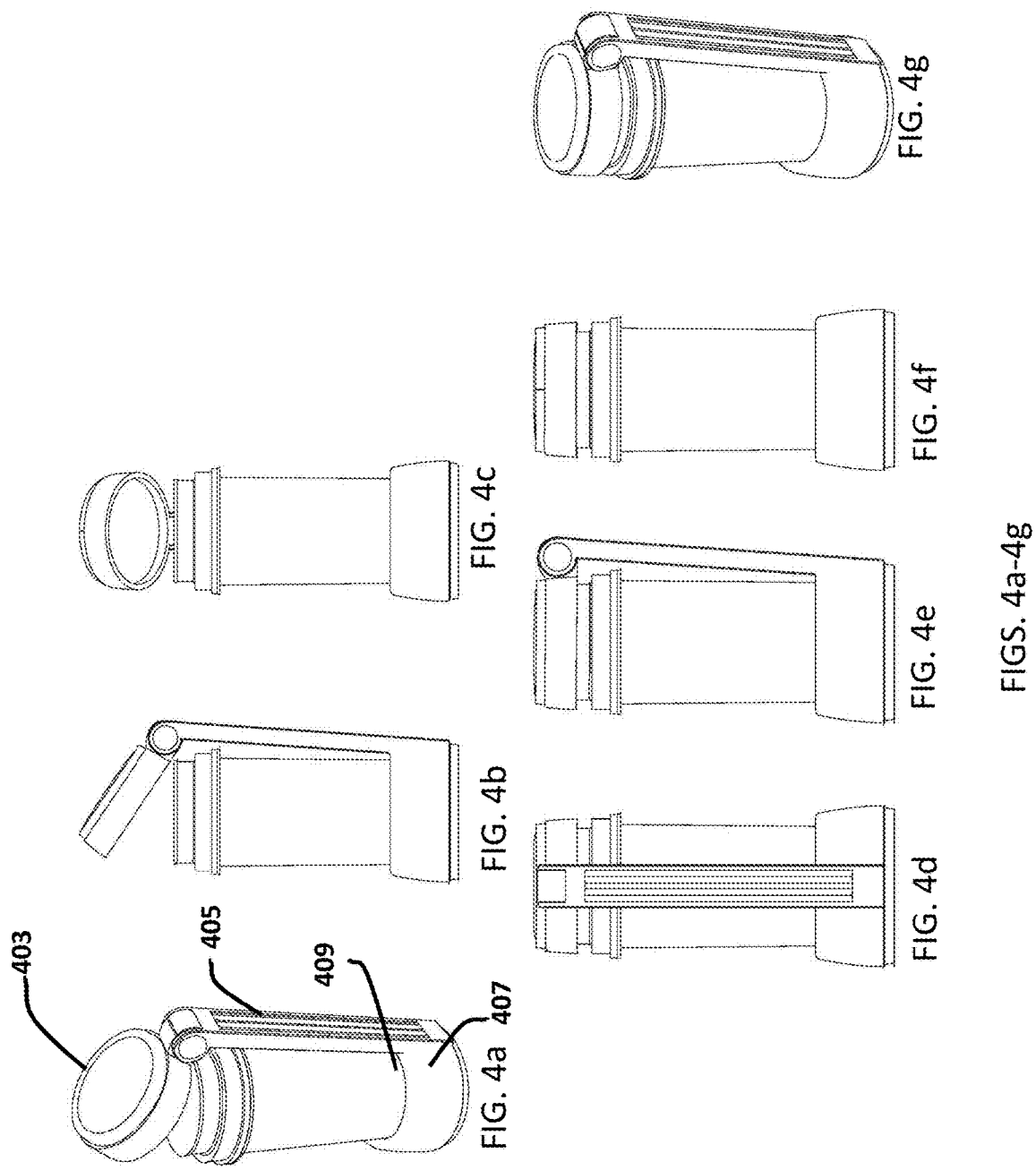
FIGS. 4a-4g provide perspective views of a medication-taking status monitoring apparatus, according to one aspect of the present disclosure.

FIGS. 4a-4g provide perspective views of an apparatus for monitoring medication-taking status according to another aspect of the present disclosure. FIG. 4a provides a side view of the apparatus for monitoring medication-taking status. According to one aspect of the disclosure, the apparatus includes a lid 403, a base 407 and a medication container adaptor 405 coupling the lid 403 with the base 407. Fitting between the lid 403 and the base 407 is a medication container 409. The medication container adaptor 405 may include an extendible support so that medication containers of different sizes may fit between the lid 403 and the base 407. In one aspect, the extendible support of the adaptor 405 may be a handle and contains a wire connecting the lid 403 to the base 407. In an alternative embodiment, the lid 403 may communicate with the base 407 via a wireless link. The lid 403 and base 407 may both include coupling mechanisms to allow easy fitting of the medication container 409 between the lid 403 and the base 407. One of the coupling mechanisms is a silicon ring that can accommodate different shapes of the medication container 409.

FIG. 4a shows a side perspective view of the apparatus with the lid 403 open. FIGS. 4b-4c show another side view and a front view of the apparatus with the lid open. FIG. 4d shows a back view of the apparatus with the lid closed, FIG. 4e a side view, FIG. 4f a front view, and FIG. 4g another side view of the apparatus with the lid closed.

Figure 5:
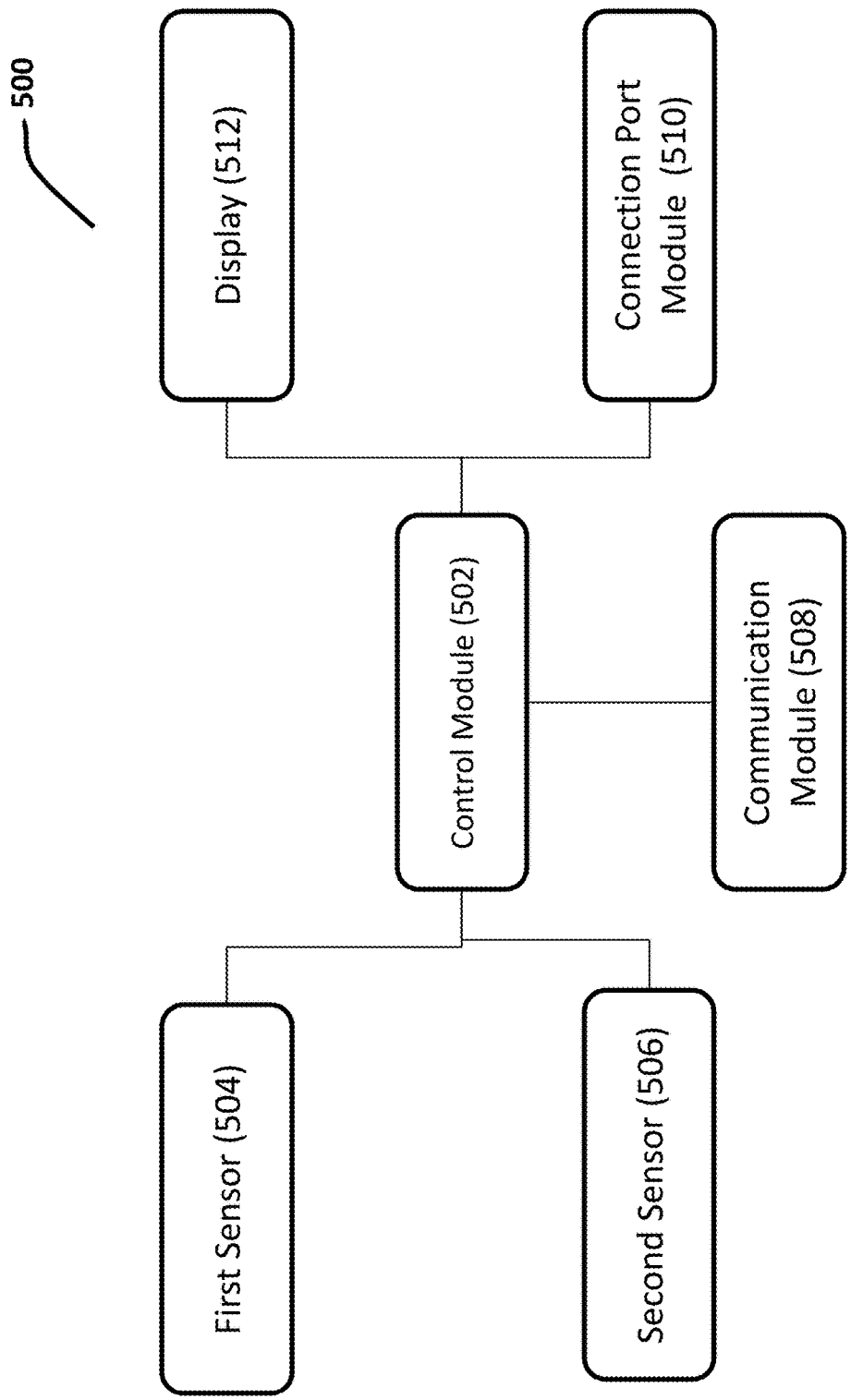
FIG. 5 provides a block diagram illustrating components of a medication-taking status monitoring apparatus, according to one aspect of the present disclosure.

FIG. 5 provides a block diagram for a logical view of the components of a medication-taking status monitoring apparatus 500, according to one aspect of the present disclosure. The medication-taking status monitoring apparatus 500 may include a control module 502, a first sensor 504, a second sensor 506, and a communication module 508. The medication-taking status monitoring apparatus 500 may also include a connection port module 510 and a display 512.

The first sensor may be one of a variety of sensor types. For example, the first sensor may be a light and color sensor for coloring detection to distinguish colors of different types of medications. In one example aspect, the first sensor may be a 2-D or 3-D shape detector to detect shapes of medications in a medication container. The medication may include traditional pills, capsules, tablets, caplets, and the like. The first sensor is configured to distinguish traditional pills from capsules or other forms of medication.

In another example aspect, the first sensor 504 is a micro-weight sensor that is sensitive to the level of milligram. As such, the first sensor is configured to accurately measure the weight of medication pills in the medication container to a level of single pill, no matter how small the pill is. Advantages of the first sensor 504 configured as a micro-weight sensor include the simplicity and accuracy. By comparing the weight of the medications in the medication container, the medication-taking status monitoring apparatus 500 is oblivious to a variety of shapes and colors of medications and can still accurately determine the medication-taking status.

As illustrated in FIGS. 1-3, the first sensor 504 may be located or disposed inside the cap or base of a medication container, such as in medication containers 100, 200, and 300. In another example aspect, the first sensor 504 may be disposed inside the lid 403, the adaptor 405 or the base 407 of the apparatus as shown in FIG. 4a. The first sensor 504 is configured to communicate with the control module 502 to follow a command to activate or deactivate itself, to communicate the measurement results to the control module 502 via a wired or wireless link.

The second sensor 506 may be different from and complement the first sensor. In one example aspect, the second sensor is a gyro sensor to detect a motion of the attached medication container 500. A gyro sensor is also known as angular rate sensor or angular velocity sensor that senses angular velocity. That is, angular velocity is the change in rotational angle per unit of time and angular velocity is generally expressed in degrees per second.

As illustrated in FIGS. 1-3, the second sensor 506 may be located or disposed inside the cap or the base of a medication container, such as the medication containers 100, 200, and 300. In another example aspect, the second sensor 506 may be disposed inside the lid 403, the adaptor or the base 407 of the apparatus as shown in FIG. 4a. The second sensor 506 is configured to communicate with a control module 502 to communicate the measurement results to the control module 502.

The communication module 508 may include one or more wireless transceivers such as a Wi-Fi transceiver, a Bluetooth transceiver or a near field radio transceiver. The communication module 508 may also include a wired transceiver and wired connection. The communication module 508 may communicate with a local wireless server such as a Wi-Fi access point and/or a Bluetooth master radio that is located outside the medication container. In one configuration of the medication container, such as the one shown in FIG. 1, one part of the communication module located on the cap of the medication container may communicate with the other part of the communication module located at the base of the medication container, via either a wireless link or wired link. In an example scenario, a wired link is used for communications between the part of communication module at the cap of the medication container and the part of the communication module at the base of the medication container. The wired link may be embedded in the wall of the medication container, or in the adaptor 405 of FIG. 4a, invisible to the user.

The connection port module 510 may include one or more connection ports. The connection ports may include one or more of a serial port, a USB port, an audio port or a wireless receiving port. The one or more ports may allow a user to plug in various measurement devices. The measurement devices may include, but are not limited to, a blood pressure measurement device, a blood glucose level measurement device, a body temperature thermostat, a body weight and body composition measurement device, a lung function testing spirometer device, and an electrocardiography (ECG) device. The connection port module 510 may read data from the plugged-in measurement devices and send the data to the control module 502. The connection port module 510 may be disposed on the outside of the base 106 of FIG. 1 or base 206 of FIG. 3 according to one example aspect of the disclosure. According to another example aspect of the disclosure, the connection port module 510 may be disposed on the outside of the lid 403, the adaptor 405 or the base 407 of FIG. 4a.

The display 512 may be a LED display disposed on the outside surface of the cap or base of the medication container, or on the lid 403 of FIG. 4a. The display 512 may receive a command from the control module 502 and displays a warning message or reminder text based on the determined medication-taking status.

The control module 502 may be configured to determine the medication-taking status based on measurements from the first sensor 504. The control module 502 may further determine whether the medication-taking status is in accordance with an active prescription stored in a local memory and to give a warning indicator if the medication-taking status is not in accordance with the active prescription. The warning indicator may include a warning buzzer, a warning light, and a warning message.

The control module 502 may further receive one or more prescriptions or medication regiments from a user. The one or more prescriptions may be downloaded into the medication container via a manual input from input keys located on an outer surface of the medication container. The one or more prescriptions may be downloaded into the medication container from a server in a network cloud or an application on a mobile device. The control module 502 may also store the one or more prescriptions in the local memory, and allow a user to set one of the stored one or more prescriptions as an active prescription for the medication pills presently stored in the medication container. In one example aspect, the control module, embodied in both software and hardware, may reside in the lid 403, the adaptor 405 or the base 407 of FIG. 4a. In another example aspect, the control module may reside in the cap or the base as shown in FIGS. 1-3.

Figure 6:
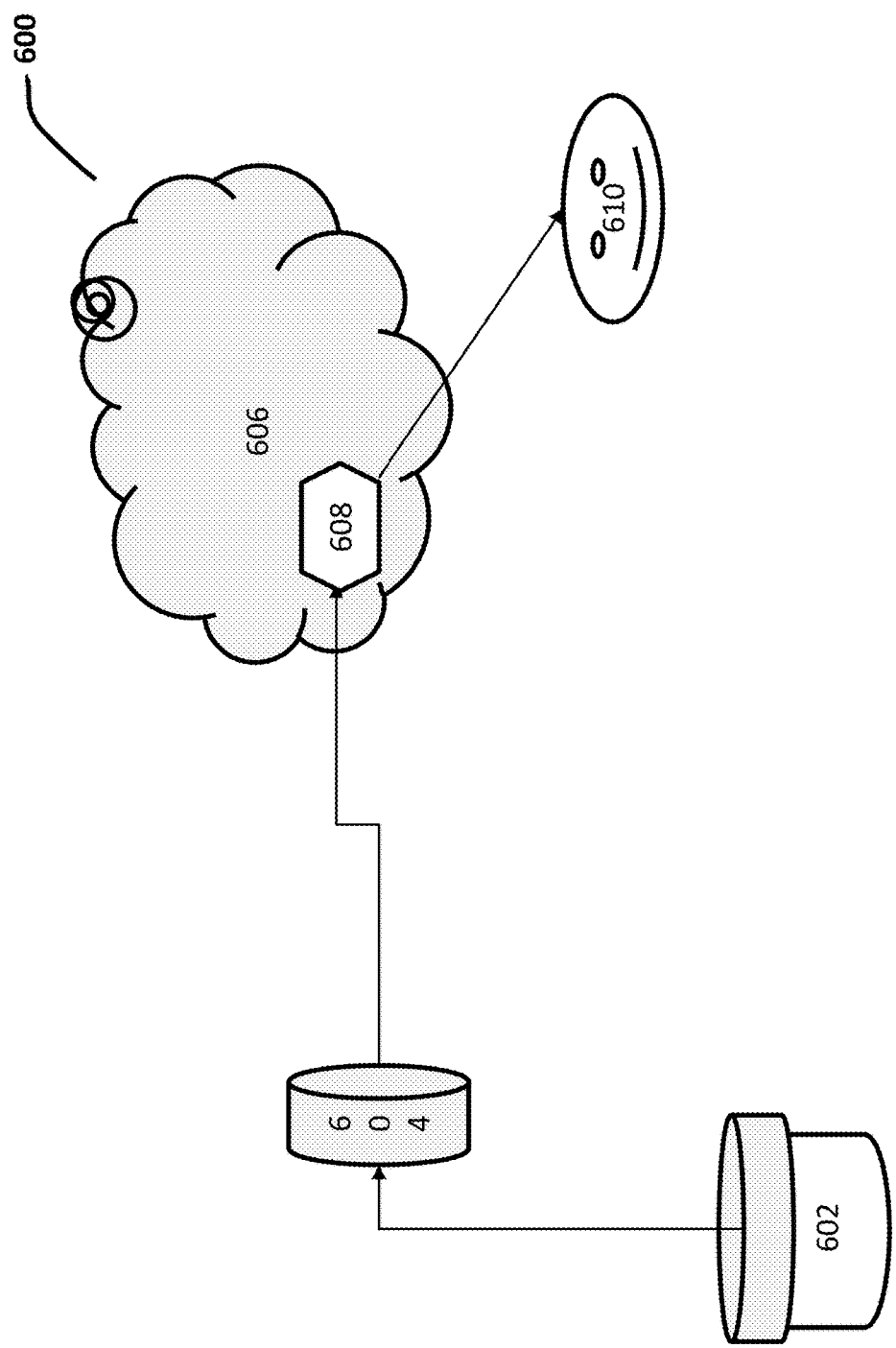
FIG. 6 provides a block diagram illustrating a network view of a medication-taking status monitoring apparatus, according to one aspect of the present disclosure.

FIG. 6 provides a network view 600 of the medication-taking status monitoring apparatus, according to one aspect of the present disclosure. The network view 600 includes a medication container 602, a local wireless server 604, a network cloud 606, a remote server 608 in the network cloud 606, and a remote subscriber 610 connected to the remote server via the network cloud 606. The medication container 602 may send a report or a warning message to and receive data from the remote server 608 via the local wireless server 604. The remote server 608 may forward the report or warning message to the remote subscriber 610. The remote subscriber 610 may be a family member, a medical professional such as a nurse or a doctor, or an elderly care monitoring professional.

Figure 7:
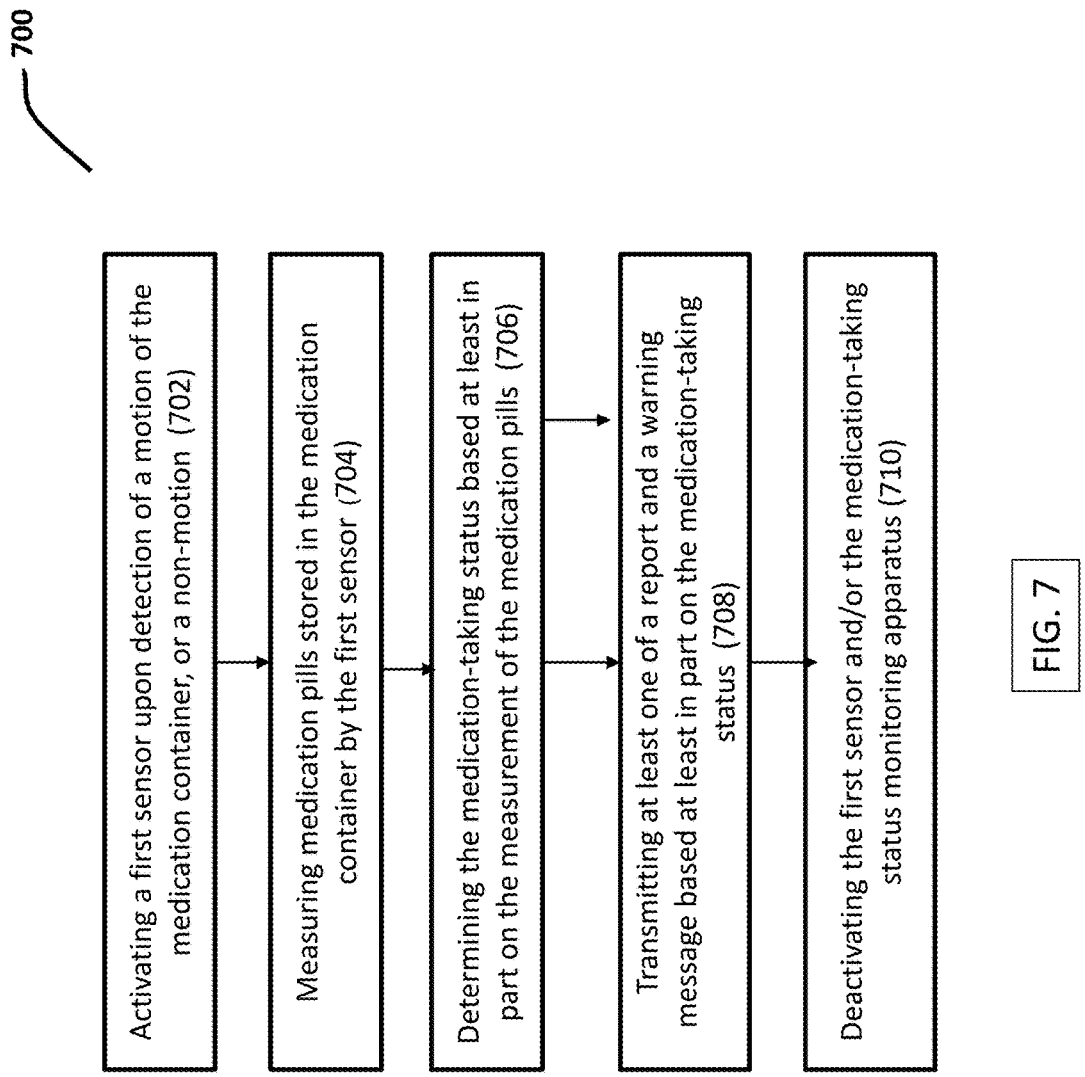
FIG. 7 provides a block diagram illustrating a method for monitoring a medication-taking status according to one aspect of the present disclosure.

FIG. 7 provides a block diagram illustrating an example method 700 for monitoring medication-taking status according to one aspect of the present disclosure. The method 700 includes activating a first sensor upon detection of a motion of the medication container at block 702. Activating the first sensor may include turning on the power of the first sensor and readying it for operations. In one example aspect, a triggering event for activating the first sensor is detection of the motion of the attached medication container. A second sensor, such as a gyro sensor, is responsible for detecting the motion of the medication container. In one example scenario, when the user of the medication container picks up the medication container and takes one or more medication pills from the medication container, the second sensor detects the motion of the medication container and the activation of the first sensor is triggered.

In another example aspect, the gyro sensor may be configured to detect non-motion. The first sensor is activated after a predefined time period of non-motion. For example, when a predefined time period, say, 12 hours, has passed, the second sensor fails to detect any motion of the medication container, the first sensor is also activated to measure the medication pills in the medication container.

The example method 700 also includes measuring medication pills stored in the medication container at block 704 by the first sensor upon the activation of the first sensor. In one example aspect, measuring the medication pills includes weighing the medication pills stored in the medication container and determining a current weight of the medication pills with a micro weight sensor that is sensitive to the level of milligrams. In other example aspect, measuring the medication pills may include counting the medication pills based in part on the shapes and colors of the medication pills.

The method 700 also includes determining a medication-taking status based at least in part on the measurements of the medication pills at block 706. Determining the medication-taking status may include determine whether any medication pills have been taken and how many have been taken, during a specified time period or duration. For example, a control module of the medication-taking status monitoring apparatus, such as the control module 502 of FIG. 5, may compare the measured weight of the current load in the medication container against that of the previous weight. If the two weights are the same, it indicates that the user has not taken any medication for the time period between the two measurements. If the two weights are different, the number of medication pills that have been taken may be determined based on the difference of the two measurements. In another example aspect, the control module may determine the medication-taking status based on a count of medication pills or other measurements.

The method 700 also includes transmitting a report at block 708 to at least one remote subscriber. The report may be transmitted to the remote subscriber on a scheduled basis, such as a daily basis. The report may also be transmitted on an on-demand, real-time basis, at a requested by the remote subscriber. The report may include a variety of information. For example, the report may include information related to medication taking status and the data from one or more plugged in measurement devices. For example, the report may include the medication-taking status, a medication-taking time, and data from the first sensor and the second sensor. If the user also plugged in one or more external devices into the connection port module, as described above, the report may also include data from the blood pressure measurement device, data from the blood glucose level measurement device, data from the body temperature thermostat, data from the body weight and body composition measurement device, data from the lung function testing spirometer device, and data from the ECG device. The report may also include a unique identifier enabling the remote server in a network cloud to associate the data with the user to protect privacy of the user.

In one example aspect, the method 700 also includes transmitting a warning message at block 708 to at least one remote subscriber. The warning message may be triggered when the determined medication-taking status indicates that the user fails to take the medication within a specified time period, such as 24-hour or 48-hour period. The time period may be set by the user of the medication container or the remote subscriber. The warning message in general may include less information than the report as described above. In one example aspect, the warning message may include the medication-taking status indicating that the user has failed to take any medication within the prescribed time period and a unique identifier to protect the user's privacy. In another example aspect, either the remote subscriber or the user may configure the contents of the report and the warning message.

The method 700 may also include deactivating the first sensor at block 710. The first sensor may be a low-power sensor. To conserve the power, the first sensor is turned on when it is to perform the measurement. The first sensor may be deactivated automatically after a predefined time period of inactivity. The apparatus itself may be deactivated when the user presses an on/off button that is disposed on the surface of the medication container.

The method 700 of FIG. 7 illustrates one example process for monitoring the medication-taking status. The steps of the method 700 and the sequence of the steps are for illustration purpose. Different sequences and additional or alternative steps are certainly possible. As such, the method 700 is a non-limiting example method for monitoring the medication-taking status.

Figure 8:
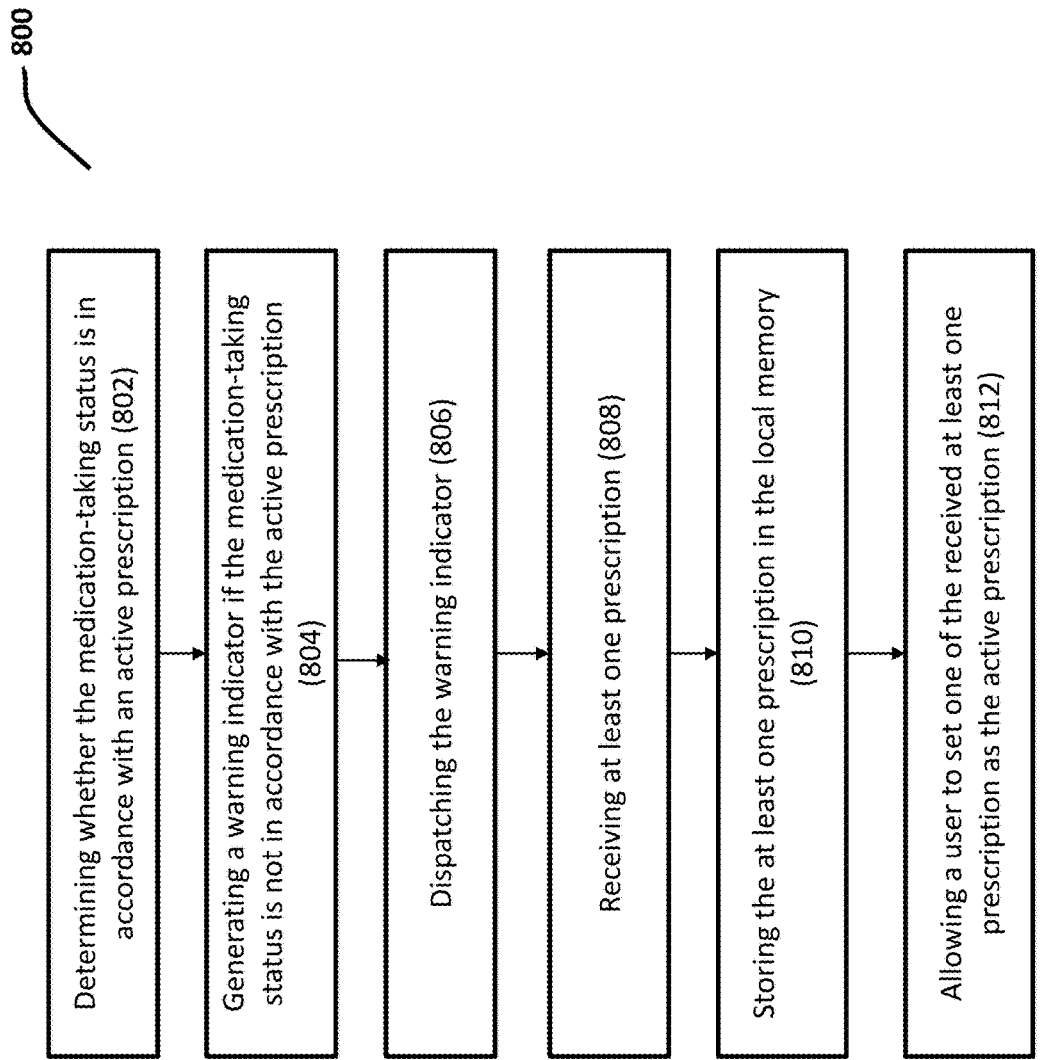
FIG. 8 provides a block diagram illustrating another method related to an active prescription for monitoring a medication-taking status according to one aspect of the present disclosure.

FIG. 8 provides another block diagram illustrating a method related to an active prescription for monitoring medication-taking status according to one aspect of the present disclosure. The method 800 may include determining at block 802 whether the medication-taking status is in accordance with an active prescription. The active prescription may indicate a dosage and other related medication regiment information. Determining whether the medication-taking status is in accordance with an active prescription at block 802 may include comparing the medication-taking status information against the active prescription and determining whether the medication-taking status follows the active prescription. The determining also includes allowing certain margin of errors. For example, if the time period as indicated in the medication-taking status exceeds the time period of the active prescription, but within a predefined margin, the medication-taking status is still viewed as being in accordance with the active prescription.

The method 800 may also include generating a warning indicator at block 804 if the medication-taking status is not in accordance with the active prescription. The warning indicator may include a warning buzzer, a warning light, or a warning message. Generating the warning indicator may include generating one or more appropriate warning indicators based on the difference between the medication-taking status and the active prescription. For example, if the user is a little late in taking the medication, a warning buzzer and/or a warning light may be sufficient. As another example, if the user took double amount of medication than prescribed, it may be appropriate to send a warning message to the remote subscriber, who may check on the patient user.

The method 800 may also include dispatching a warning indicator at block 806. Dispatching the warning indicator may include displaying a warning light on a display located on the cap or the base of the medication container, emitting a buzzing sound, or transmitting a warning message to the remote subscriber. The method 800 may also include receiving at least one prescription at block 808. Receiving one or more prescriptions may include receiving one or more prescriptions via a manual input from input keys located at an outer surface of the medication container, a download from the remote server in a network cloud or an application on a mobile device. The method 800 may also include storing the received one or more prescriptions in a local memory at block 810 and allowing the user to set one of the received one or more prescriptions as the active prescription at block 812.

The method 800 of FIG. 8 illustrates one example process related to the currently active prescription for monitoring medication-taking status. The steps of the method 800 and the sequences of the steps are for illustration. Different sequences of the steps and additional or alternative steps are certainly possible. As such, the method 800 is a non-limiting example method for monitoring the medication-taking status.

Figure 9:
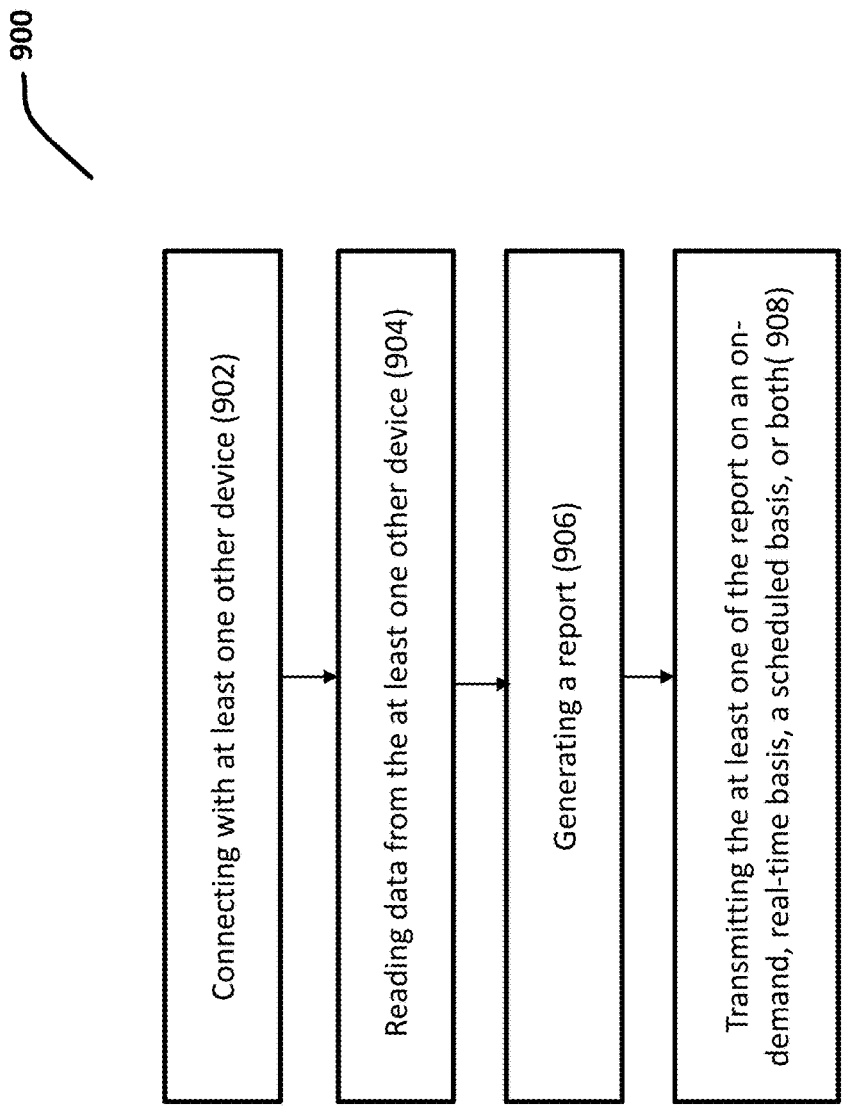
FIG. 9 provides a block diagram illustrating yet another method for monitoring a medication-taking status according to one aspect of the present disclosure.

FIG. 9 provides a block diagram illustrating yet another method for monitoring medication-taking status according to one aspect of the present disclosure. The method 900 may include connecting with at least one other device at block 902 and reading data from the at least one other device at block 904. Connecting wither the at least one other device may include recognizing one or more measurement devices that are plugged into the connection port module as illustrated in FIG. 5. Reading data from the at least one other device at block 904 include reading data from the plugged-in devices. The other devices may include a blood pressure measurement device, a blood glucose level measurement device, a body temperature thermostat, a body weight and body composition measurement device, a lung function testing spirometer device, and an ECG device. The method 900 may also include generating a report at block 906, based on the medication-taking status and data from the other measurement devices. The method 900 may further include transmitting the generated report at block 908 on an on-demand, real-time basis, on a scheduled basis, or both.

The method 900 of FIG. 9 illustrates one example process for monitoring the medication-taking status. The steps of the method 900 and the sequences of the steps are for illustration. Different sequences of the steps and additional or alternative steps are certainly possible. As such, the method 900 is a non-limiting example method for monitoring the medication-taking status.

Those of skill would further appreciate that the various illustrative logical blocks, modules, circuits, and algorithm steps described in connection with the disclosure herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the disclosure herein may be implemented or performed with a general-purpose processor, a special-purpose sensor, an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine.

The steps of a method or algorithm described in connection with the disclosure herein may be embodied directly in hardware, in a software module executed by a processor, or in a combination of the two. A software module may reside in RAM memory, flash memory, ROM memory, EPROM memory, EEPROM memory, registers, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a sensor device. In the alternative, the processor and the storage medium may reside as discrete components in a sensor device.

In one or more exemplary designs, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, or other optical disk storage, or any other medium that can be used to carry or store desired program code means in the form of instructions or data structures. Also, any connection is properly termed a computer-readable medium. For example, if the software is transmitted from a website, a remote server in a network cloud, or other remote source using a wired link such as a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Combinations of the above should also be included within the scope of computer-readable media.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein but is to be accorded the widest scope consistent with the principles and novel features disclosed herein.

What is claimed is:

1. An apparatus for monitoring a medication-taking status, configured as a part of or
    coupled with a medication container, comprising:
    a first sensor that is disposed inside the apparatus, activated upon a detection by a second sensor of a motion of the medication container, or a non-motion of the medication container for a predefined time period, and configured to measure medication pills stored in the medication container;
    a control module configured
        to determine the medication-taking status based on the measurement of the medication pills; and
    a communication module that is disposed inside the apparatus and configured to transmit at least one of a report and a warning message based at least in part on the medication-taking status to at least one remote subscriber,
    wherein the first sensor is deactivated after a predetermined period of inactivity and the apparatus is activated when an activation button is pressed, the activation button being disposed on an outer surface of the apparatus; and wherein the second sensor comprises a gyro sensor configured to detect the motion or non-motion of the medication container, the gyro sensor being disposed inside the apparatus.

2. The apparatus of claim 1, wherein the medication-taking status comprises whether any of the medication pills has been taken and how many of the medication pills have been taken within a prescribed time period.

3. The apparatus of claim 1, wherein the first sensor comprises a micro weight sensor and is configured to measure a weight of the medication pills; and wherein determining the medication taking status is based on the measured weight of the medication pills.

4. The apparatus of claim 1, wherein the control module is configured to determine whether the medication-taking status is in accordance with an active prescription stored in a local memory and to give a warning indicator if the medication-taking status is not in accordance with the active prescription, the warning indicator comprising at least one of a warning buzzer, a warning light, and the warning message; and wherein the control module is further configured to receive at least one prescription via a manual input from input keys disposed on an outer surface of the apparatus, a download from a remote server in a network cloud or an application on a mobile device, to store the at least one prescription in the local memory, and to allow a user to set one of the received at least one prescription as the active prescription.

5. The apparatus of claim 4, wherein the apparatus is coupled with the medication container via an adaptor, a lid and a base, the adaptor comprising an extendible support to accommodate different sizes of the medication container, and connecting the lid to the base of the apparatus;
    wherein the first sensor, the second sensor, the control module, and the communication module are disposed inside at least one of the lid, the adaptor, and the base of the apparatus; and wherein the warning light or the warning buzzer is displayed or played on one of the lid and the base, and the lid and the base communicate with each other via a wired or wireless link.

6. The apparatus of claim 1, wherein the apparatus is configured as a cap, a base, or both of the medication container, the apparatus is coupled with a body of the medication container via a coupling mechanism comprising one or more of: coupling threads, a clip-on container-cap lock, a silicon holding ring, and a coupling clinch; and
    wherein the warning light or the warning buzzer is displayed or played on one of the cap and the base of the medication container, and the cap and base of the medication container communicate with each other via a wired or wireless link when the apparatus comprises both the cap and the base of the medication container.

7. The apparatus of claim 1, further comprising at least one connection port disposed on an outer surface of the apparatus, configured to connect with and read data via a wireless or wired connection from at least one of: a blood pressure measurement device, a blood glucose level measurement device, a body temperature thermostat, a body weight and body composition measurement device, a lung function testing spirometer device, and an electrocardiography (ECG) device, wherein the at least one connection port comprises at least one of a serial port, a Universal Serial Bus (USB) port, and an audio port, and the wired connection comprises one of a micro USB connection and a mini USB connection.

8. The apparatus of claim 7, wherein the report and the warning message comprises at least one of: the medication-taking status, a medication-taking time, data from the first sensor and the second sensor, data from the blood pressure measurement device, data from the blood glucose level measurement device, data from the body temperature thermostat, data from the body weight and body composition measurement device, data from the lung function testing spirometer device, data from the ECG device, and a unique identifier enabling a remote server in a network cloud to associate the data with a user to protect privacy of the user.

9. The apparatus of claim 8, wherein the warning message and the report are sent to the at least one remote subscriber in part on a wireless communication link on a real-time on-demand basis, a scheduled basis, or both; and wherein the wireless communication link is based on at least one of: a WiFi system, a Bluetooth system, a near-field wireless communication system, and a cellular wireless communication system.

10. A method for monitoring a medication-taking status by a monitoring apparatus, the monitoring apparatus configured as part of or coupled with a medication container, comprising:
  activating a first sensor upon detection by a second sensor of a motion of the medication container, or a non-motion of the medication container for a predefined time period;
  measuring medication pills stored in the medication container by the first sensor upon activation of the first sensor;
  determining the medication-taking status based at least in part on the measurement of the medication pills by the first sensor; and
  transmitting at least one of a report and a warning message based at least in part on the medication-taking status to at least one remote subscriber,
  wherein the first sensor is deactivated after a predetermined period of inactivity and the apparatus is activated when an activation button is pressed, the activation button being disposed on an outer surface of the apparatus; and wherein the second sensor comprises a gyro sensor configured to detect the motion or non-motion of the medication container, the gyro sensor being disposed inside the apparatus.

11. The method of claim 10, wherein the medication-taking status comprises whether any of the medication pills has been taken and how many of the medication pills have been taken within a prescribed period; wherein the first sensor comprises a micro weight sensor and is configured to measure a weight of the medication pills; and wherein the determination of the medication taking status is based on the measured weight of the medication pills.

12. The method of claim 10, further comprising determining whether the medication-taking status is in accordance with an active prescription stored in a local memory; giving a warning indicator if the medication-taking status is not in accordance with the active prescription, the warning indicator comprising at least one of a warning buzzer, a warning light, and the warning message; displaying the warning indicator on a cap of the medication container when the monitoring apparatus is configured as the cap, a base or both of the medication container wherein at least one of the first sensor, the second sensor, and a control module is disposed inside at least one of the base and the cap of the medication container, and the base and the cap communicate with each other via a wired or wireless link; displaying the warning indicator on a lid of the monitoring apparatus when the monitoring apparatus is coupled with the medication container, via an adaptor, the lid and a second base, the adaptor comprising an extendible support to accommodate different sizes of the medication container, and connecting the lid to the second base of the apparatus; wherein the first sensor, the second sensor, the control module, and the communication module are disposed inside at least one of the lid, the adaptor and the second base of the apparatus; and wherein the lid and the base communicate with each other via the wired or wireless link; receiving at least one prescription via a manual input from input keys disposed on an outer surface of the monitoring apparatus, a download from a remote server in a network cloud or an application on a mobile device; storing the at least one prescription in the local memory, and allowing a user to set one of the received at least one prescription as the active prescription.

13. The method of claim 12, further comprising deactivating the first sensor after a predetermined period of inactivity; and activating or deactivating the monitoring apparatus upon pressing of an activation button by the user, wherein the activation button is located on an outer surface of the monitoring apparatus.

14. The method of claim 10, further comprising connecting with and reading data via at least one connection port disposed on an outer surface of the monitoring apparatus and a wired or wireless connection from at least one of:
  a blood pressure measurement device, a blood glucose level measurement device, a body temperature thermostat, a body weight and body composition measurement device, a lung function testing spirometer device, and an electrocardiography (ECG) device, wherein the at least one connection port comprises at least one of a serial port, a USB port, and an audio port,
  and the wired connection comprises one of a micro USB connection and a mini USB connection; and
  generating the report and the warning message comprising at least one of: the medication-taking status, a medication-taking time, data from the first sensor and the second sensor, data from the blood pressure measurement device, data from the blood glucose level measurement device, data from the body temperature thermostat, data from the body weight and body composition measurement device, data from the lung function testing spirometer device, data from the ECG device, and a unique identifier enabling a remote server in a network cloud to associate the data with a user to protect privacy of the user.

15. The method of claim 10, wherein the transmitting of the at least one of the report and the warning message further comprises transmitting the at least one of the report and the warning message on a wireless communication link on an on-demand real-time basis, a scheduled basis, or both.

16. An apparatus for monitoring a medication-taking status, the apparatus configured as part of or coupled with a medication container, comprising:
  a memory; and at least one processor coupled to the memory and configured to: activate a first sensor upon detection by a second sensor of a motion of the medication container, or a non-motion of the medication container for a predefined time period;

measure medication pills stored in the medication container by the first sensor upon activation of the first sensor;

determine the medication-taking status based at least in part on the measurement of the medication pills from the first sensor; and transmit at least one of a report and a warning message based at least in part on the medication-taking status to at least one remote subscriber, wherein the first sensor is deactivated after a predetermined period of inactivity and the apparatus is activated when an activation button is pressed, the activation button being disposed on an outer surface of the apparatus; and wherein the second sensor comprises a gyro sensor configured to detect the motion or non-motion of the medication container, the gyro sensor being disposed inside the apparatus.

17. The apparatus of claim 16, wherein the medication-taking status comprises whether any of the medication pills has been taken and how many of the medication pills have been taken within a prescribed period; wherein the first sensor comprises a micro weight sensor and is configured to measure a weight of the medication pills in the medication container; and wherein the determination of the medication-taking status is based on the measured weight of the medication pills.

18. The apparatus of claim 16, wherein the at least one processor is further configured to determine whether the medication-taking status is in accordance with an active prescription stored in a local memory;

give a warning indicator if the medication-taking status is not in accordance with the active prescription, the warning indicator comprising at least one of a warning buzzer, a warning light, and the warning message;

display the warning indicator on a cap of the medication container when the apparatus is configured as the cap, a base or both of the medication container wherein at least one of the first sensor, the second sensor, and a control module is disposed on one of the cap and the base of the medication container, and the cap and the base of the medication container communicate with each other via a wired or wireless link;

display the warning indicator on a lid of the apparatus when the monitoring apparatus is coupled with the medication container, via an adaptor, the lid and a second base, the adaptor comprising an extendible support to accommodate different sizes of the medication container, and connecting the lid to the second base of the apparatus; wherein the first sensor, the second sensor, the control module, and the communication module are disposed inside at least one of the lid, the adaptor, and the second base of the apparatus; and wherein the lid and the base communicate with each other via the wired or wireless link;

receive at least one prescription via a manual input from input keys disposed on an outer surface of the apparatus, a download from a remote server in a network cloud or an application on a mobile device;

store the at least one prescription in the local memory, and allow a user to set one of the received at least one prescription as the active prescription.

19. The apparatus of claim 18, wherein the at least one processor is further configured to deactivate the first sensor after a predetermined period of inactivity; and activate or deactivate the apparatus upon pressing of an activation button by the user, wherein the activation button is located on an outer surface of the monitoring apparatus.

* * * * *